United States Patent
Kahn et al.

(10) Patent No.: US 6,322,978 B1
(45) Date of Patent: Nov. 27, 2001

(54) REPEAT POLYMORPHISM IN THE FRATAXIN GENE AND USES THEREFORE

(75) Inventors: C. Ronald Kahn, West Newton; Michael Ristow, Boston, both of MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 09/292,487

(22) Filed: Apr. 15, 1999

Related U.S. Application Data
(60) Provisional application No. 60/082,369, filed on Apr. 20, 1998.

(51) Int. Cl.[7] .............. C12Q 1/68; C07H 21/04; C12P 19/34
(52) U.S. Cl. .............. 435/6; 536/24.31; 536/24.33; 435/91.2; 435/91.5
(58) Field of Search .............. 435/6; 563/24.31; 536/24.31, 24.33

(56) References Cited

U.S. PATENT DOCUMENTS 5,470,839  11/1995  Laughlin et al. .............. 514/53
5,871,769  2/1999  Fleming et al. .............. 424/423

OTHER PUBLICATIONS

Epplen, et al., Jun. 10, 1997. Human Genetics 99:834–836.*
Cossee, et al., Jul. 1997. Proc Natl Acad Sci, 94:7452–7457.*
Encyclopaedia Britannica Online. Diabetes. Feb. 7, 2001.*
Bidichandani et al. (1998) "The GAA Triplet–Repeat Expansion in Friedreich Ataxia Interferes with Transcription and May Be Associated with an Unusual DNA Structure", *Am. J. Human Genet.* 62:111–121.
Campuzano et al. (1997) "Frataxin is Reduced in Friedreich Ataxia Patients and is Associated with Mitochondrial Membranes", *Human Mol. Genet.* 6(11):1771–1780.
Montermini et al. (1997) "The Friedreich Ataxia GAA triplet Repeat: Premutation and Normal Alleles", *Human Mol. Genet.* 6(8):1261–1266.

* cited by examiner

*Primary Examiner*—Robert A. Schwartzman
*Assistant Examiner*—Q Janice Li
(74) *Attorney, Agent, or Firm*—Fish & Richardson P.C.

(57) ABSTRACT

The invention provides methods of determining whether a subject is at risk for a disorder characterized by an intermediate GAA repeat length polymorphism in the frataxin gene.

16 Claims, 2 Drawing Sheets

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: primer for PCR

<400> SEQUENCE: 1
ggcttaaact tcccacacgt gtt                                           23

<210> SEQ ID NO 2
<211> LENGTH: 21
<212> TYPE: DNA
<213> ORGANISM: Artificial Sequence
<220> FEATURE:
<223> OTHER INFORMATION: primer for PCR

<400> SEQUENCE: 2
aggaccatca tggccacact t                                             21

REPEAT POLYMORPHISM IN THE FRATAXIN GENE AND USES THEREFORE

CROSS REFERENCE TO RELATED APPLICATIONS

This application claims the benefit from U.S. Provisional Application No. 60/082,369, filed Apr. 20, 1998.

FIELD OF THE INVENTION

This invention relates to a frataxin intermediate GAA repeat length polymorphism and uses therefore, e.g., genetic screening of subjects at risk for non insulin diabetes mellitus.

BACKGROUND OF THE INVENTION

Non insulin diabetes mellitus (NIDDM) is a clinically heterogeneous disorder (Kahn, C. R. (1994) *Diabetes* 43:1066–1084) characterized by insulin resistance in peripheral tissues combined with impaired insulin secretion of the pancreatic β-cell (DeFronzo, R. A. et al. (1992) *Diabetes Care* 15:318–368). Investigations of candidate genes for NIDDM have led to the identification of polymorphisms of several genes encoding proteins of insulin action and insulin secretion, but none show a high frequency of association with the disease (Kahn, C. R. et al. (1996) *Annu. Rev. Med.* 47:509–531; McCarthy, M. I. et al. (1994) *Diabetologia* 37:959–968).

Friedreich's ataxia (FRDA) is the most common hereditary ataxia (Campuzano, V. et al. (1996) *Science* 271:1423–1427), with an estimated prevalence of 1 in 50,000 people (Epplen, C. et al. (1997) *Hum. Genet.* 99:834–836). FRDA is a degenerative disease characterized by progressive ataxia, lack of tendon reflexes, loss of position sense, dysarthria, and hypertrophic cardiomyopathy. FRDA is inherited as an autosomal recessive disease. FRDA appears to belong to the family of triplet repeat disorders, including myotonic dystrophy, fragile X syndrome, and Huntington's disease (Wells, R. D. (1996) *J. Biol. Chem.* 271:2875–2878). The FRDA has been mapped to chromosome 9q13-q21 (Hanauer, A. et al. (1990) *Am. J. Hum. Genet.* 46:133–137) and attributed to a GAA triplet repeat expansion (McCarthy, M. I. et al. (1994) *Diabetologia* 37:959–968) in the frataxin gene, also known as X25 or STM7. Frataxin encodes a protein, which is targeted to the mitochondria and has been suggested to function as an endogenous antioxidant (Rotig, A. et al. (1997) *Nat. Genet.* 17:215–217).

SUMMARY OF THE INVENTION

In general, the invention features, a method for determining whether a subject is at risk for a disorder characterized by an intermediate GAA repeat length polymorphism in the frataxin gene. The method includes: obtaining a biological sample from the subject; and detecting the presence or absence of an intermediate GAA repeat length polymorphism in frataxin nucleic acid in the biological sample e.g. in genomic DNA, thereby determining whether the subject is at risk for a disorder characterized by an intermediate GAA repeat length polymorphism in the frataxin gene.

In preferred embodiments, the disorder characterized by an intermediate GAA repeat length polymorphism in the frataxin gene is diabetes, e.g., non-insulin dependent diabetes mellitus or a disorder characterized by insufficient levels of an anti-oxidant.

In preferred embodiments, the method includes isolating a nucleic acid, e.g., DNA, total RNA, or mRNA, from the biological sample. For example, mRNA can be isolated using the guanidinium-thiocyanate extraction procedure of Chirgwin et al. (1979) *Biochemistry* 18: 5294–5299.

In preferred embodiments, the presence or absence of an intermediate GAA repeat length polymorphism in the frataxin gene is detected by the use of a polymerase chain reaction, e.g., by the use of primers which can hybridize to a frataxin gene containing an intermediate length GAA repeat and e.g., produce a product characteristic of the presences of the intermediate GAA repeat.

In preferred embodiments, the presence or absence of an intermediate GAA repeat length polymorphism in the frataxin gene is detected by an alteration in a restriction enzyme cleavage pattern. For example, DNA can be isolated from a biological sample, cleaved with one or more restriction enzymes, and then compared to a control for the pattern of migration on a gel, e.g., an agarose gel.

In preferred embodiments, the presence or absence of an intermediate GAA repeat length polymorphism in the frataxin gene is detected by nucleic acid sequencing, e.g., DNA sequencing. Examples of sequencing reactions include those based on techniques developed by Maxam and Gilbert ((1977) *PNAS* 74:560) or Sanger ((1977) *PNAS* 74:5463). A variety of automated sequencing procedures can also be used, including sequencing by mass spectrometry (described in, for example, PCT International Publication No. WO 94/16101; Cohen et al. (1996) *Adv. Chromatogr.* 36:127–162; and Griffin et al. (1993) *Appl. Biochem. Biotechnol* 38:147–159).

In preferred embodiments, the biological sample is a biological fluid, e.g., blood, plasma, cerebrospinal fluid, or urine; a tissue sample, e.g., a skin biopsy sample; or a cellular sample, e.g., a blood cell sample or a skin cell sample.

In preferred embodiments, the subject can be a human, an experimental animal, e.g., a rat or a mouse, a domestic animal, e.g., a dog, cow, sheep, pig or horse, or a non-human primate, e.g., a monkey.

In preferred embodiments the method further includes: the step of identifying an individual as at risk for NIDDM or an antioxidant-related disorder; the step of administering a second diagnostic test for NIDDM or an antioxidant-related disorder; testing the subject for insulin resistance; testing the subject for glucose tolerance.

In another aspect, the invention features, a method for detecting the presence of a frataxin intermediate GAA repeat length polymorphism in a biological sample. The method includes: contacting a biological sample with an agent capable of detecting a frataxin intermediate GAA repeat length polymorphism such that the presence of a frataxin intermediate GAA repeat length polymorphism is detected in the biological sample.

In preferred embodiments: the agent is a labeled or labelable nucleic acid probe capable of hybridizing to frataxin mRNA or DNA; the agent is a nucleic acid probe capable of amplifying a frataxin gene containing an intermediate length GAA repeat.

In another aspect, the invention features, a kit for detecting the presence of a frataxin intermediate GAA repeat length polymorphism in a biological sample including an agent capable of detecting a frataxin intermediate GAA repeat length polymorphism in a biological sample.

In preferred embodiments: the kit further includes means for determining the amount of a frataxin intermediate GAA repeat length polymorphism in the sample and means for comparing the amount of a frataxin intermediate GAA repeat length polymorphism in the sample with a standard; the agent is a nucleic acid probe capable of amplifying a frataxin gene containing an intermediate length GAA repeat.

In preferred embodiments the method further includes: the step of identifying an individual as at risk for NIDDM or an antioxidant-related disorder; the step of administering a second diagnostic test for NIDDM or an antioxidant-related disorder; testing the subject for insulin resistance; testing the subject for glucose tolerance.

In another aspect, the invention features a method for determining if a subject, e.g., a human, is at risk for NIDDM or an antioxidant-related disorder. The method includes examining the subject for the expression of the frataxin gene product, non-wild type expression or mis-expression, particularly lowered expression, and more particularly lowered but not abolished expression, being indicative of risk. Expression can be detected at the protein or mRNA level.

In preferred embodiments the method further includes: the step of identifying an individual as at risk for NIDDM or an antioxidant-related disorder; the step of administering a second diagnostic test for NIDDM or an antioxidant-related disorder; testing the subject for insulin resistance; testing the subject for glucose tolerance.

In another aspect, the invention provides a substantially pure nucleic acid having, or comprising, an intermediate GAA repeat.

In preferred embodiments, the nucleic acid further includes: the first intron of frataxin; a sequence, e.g., a genomic sequence, which encodes frataxin; preferably including the first intron of frataxin; the first intron of frataxin fused (with or with out additional interposed frataxin sequence) to a non-frataxin sequence, e.g., to a reporter sequence, e.g., lacz or green fluorescent protein encoding sequence.

In preferred embodiments, the nucleic acid encodes a vertebrate, e.g., mammalian, e.g., human frataxin or frataxin polypeptide.

In a preferred embodiment, the encoded frataxin differs in amino acid sequence at 1, 2, 3, 5, 10 or more residues, but preferably less than 15, from a wild type frataxin.

In preferred embodiments, the nucleic acid will include a transcriptional regulatory sequence, e.g. at least one of a transcriptional promoter or transcriptional enhancer sequence, operably linked to the frataxin gene sequence, e.g., to render the frataxin gene sequence suitable for use as an expression vector.

In another aspect, the invention includes: a vector including a GAA intermediate repeat nucleic acid described herein; a host cell transfected with the vector; and a method of producing a recombinant frataxin, including culturing the cell, e.g., in a cell culture medium, and isolating or identifying frataxin from the cell or from the cell culture medium.

In preferred embodiments, the nucleic acid further includes: the first intron of frataxin; a sequence, e.g., a genomic sequence, which encodes frataxin; preferably including the first intron of frataxin; the first intron of frataxin fused (with or with out additional interposed frataxin sequence) to a non-frataxin sequence, e.g., to a reporter sequence, e.g., lacz or green fluorescent protein encoding sequence.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from the frataxin gene and which can be used to determine the presence of a GAA intermediate repeat. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length. In preferred embodiments the probe or primer hybridizes: to the intermediate GAA repeat; upstream or downstream from the intermediate GAA repeat. In preferred embodiments the probe or primer can direct polymerase catalysed extension across at least part of the GAA intermediate repeat.

In another aspect, the invention features a method of evaluating a compound for the ability to modulate a parameter related to NIDDM or to a disorder characterized by an insufficiency of an anti-oxidant. The parameter can be frataxin expression, glucose uptake, insulin resistance, insulin secretion expression of a diabetes related gene, e.g., the insulin receptor, or an IRS, e.g., IRS-1 or IRS-2, growth, or cell division. The method includes contacting the compound with a cell or animal and evaluating the effect of the treatment, on a parameter related to NIDDM. This method can be performed in vitro, e.g., in a cell free system, or in vivo, in cells or in a whole animal. This method can be used to identify naturally occurring or synthetic molecules which are useful for treating a disorder related to frataxin misexpression, e.g., NIDDM, or a disorder characterized by misexpression, particularly insufficient expression, of an anti-oxidant. The compound can be a peptide or a non peptide molecule, e.g., a small molecule preferably. 500 to 5,000 molecular weight, more preferably 500 to 1,000 molecular weight, having an aromatic scaffold, e.g., a bis-amide phenol, decorated with various functional groups.

The animal or cell can be wildtype with regard to frataxin or can have a frataxin gene (e.g., a transgene) having an intermediate GAA repeat. The animal or cell can have a reporter gene molecule under the control of the frataxin parameter. The reporter can e.g., be fused to a frataxin sequence having wild type intron 1, or having an intermediate GAA repeat.

In another aspect, the invention features, a transgenic animal, e.g., a mammal, e.g., a mouse or a nonhuman primate having a transgene which includes an intermediate GAA repeat.

In preferred embodiments, the transgene further includes: the first intron of frataxin; a sequence, e.g., a genomic sequence, which encodes frataxin; the first intron of frataxin; the first intron of frataxin fused (with or with out additional interposed sequence) to a reporter sequence, e.g., lacz or green fluorescent protein encoding sequence.

In preferred embodiments the animal is a transgenic mouse.

In another aspect, the invention features, a genetically engineered cell, e.g., a mammalian, e.g., a mouse or a human or nonhuman primate cell, having a introduced into it a nucleic acid includes an intermediate GAA repeat.

In preferred embodiments, the nucleic acid further includes: the first intron of frataxin; a sequence, e.g., a genomic sequence, which encodes frataxin; the first intron of frataxin; the first intron of frataxin fused (with or with out additional interposed sequence) to a reporter sequence, e.g., lacz or green fluorescent protein encoding sequence.

In preferred embodiments the animal is a transgenic mouse.

In preferred embodiments the nucleic acid which includes an intermediate GAA repeat is integrated into the genome.

In another aspect, the invention features a method for evaluating the effect of a treatment on a transgenic cell or animal having transgene which includes an intermediate GAA repeat, e.g., the effect of the treatment on a parameter related to NIDDN or a disorder characterized by misexpression, particularly insufficient expression, of an antioxidant. The method includes administering the treatment to a cell or animal having the transgene, and evaluating the effect of the treatment on the cell or animal. The effect can be, e.g., the ability to modulate a parameter related to NIDDM or to a disorder characterized by an insufficiency of an anti-oxidant. The parameter can be frataxin expression, glucose uptake, insulin resistance, insulin secretion expression of a diabetes related gene, e.g., the insulin receptor, or an IRS, e.g., IRS-1 or IRS-2, growth, or cell division.

In another aspect, the invention features a method for treating an animal, e.g., a human, a mouse, a transgenic animal, or an animal model for a disorder related to frataxin mis-expression, e.g., NIDDM, or a disorder characterized by misexpression, particularly insufficient expression, of an anti-oxidant, including administering a therapeutically-effective amount frataxin or an antioxidant to the animal.

In another aspect, the invention features a method for treating an animal, e.g., a human, a mouse, a transgenic animal, or an animal model for a disorder related to frataxin mis-expression, e.g., NIDDM, or a disorder characterized by misexpression, particularly insufficient expression, of an anti-oxidant, including administering to the animal, cells selected, e.g., selected in vitro, for the expression of frataxin or an antioxidant.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In preferred embodiments the method further includes: the step of identifying an individual as at risk for NIDDM or an antioxidant related disorder; the step of administering a second diagnostic test for NIDDM or an antioxidant-related disorder; testing the subject for insulin resistance; testing the subject for glucose tolerance.

In another aspect, the invention features a method for treating an animal, e.g., a human, a mouse, a transgenic animal, or an animal model for a disorder related to frataxin misexpression, e.g., NIDDM, or a disorder characterized by misexpression, particularly insufficient expression, of an anti-oxidant, including administering to the animal a nucleic acid encoding frataxin or an antioxidant, or which promotes the expression of frataxin or an antioxidant, and expressing the nucleic acid.

In preferred embodiments the method further includes: the step of identifying an individual as at risk for NIDDM or an antioxidant related disorder; the step of administering a second diagnostic test for NIDDM or an antioxidant-related disorder; testing the subject for insulin resistance; testing the subject for glucose tolerance.

In another aspect, the invention features, a method of modulating the expression of a gene, e.g., a frataxin gene. The method includes: forming, by recombinant nucleic acid, or cell fusion techniques, a GAA intermediate repeat in the gene, e.g., in an intron of the gene, e.g., in the first intron of the gene.

In preferred embodiments the method further includes: the step of identifying an individual as at risk for NIDDM or an antioxidant related disorder; the step of administering a second diagnostic test for NIDDM or an antioxidant-related disorder; testing the subject for insulin resistance; testing the subject for glucose tolerance.

In another aspect, the invention features, a mammal, e.g., a nonhuman mammal, e.g., e.g., a swine, a nonhuman primate, e.g., a monkey, a goat, or a rodent, e.g., a rat or a mouse, having an exogenously introduced cell having a nucleic acid including an intermediate GAA repeat.

In preferred embodiments, the nucleic acid further includes: the first intron of frataxin; a sequence, e.g., a genomic sequence, which encodes frataxin; preferably including the first intron of frataxin; the first intron of frataxin fused (with or with out additional interposed frataxin sequence) to a non-frataxin sequence, e.g., to a reporter sequence, e.g., lacz or green fluorescent protein encoding sequence.

In another aspect, the invention features a cell, or purified preparation of cells, which include a frataxin gene with an intermediate GAA repeat, or which otherwise misexpress the frataxin gene. The cell preparation can consist of human or non human cells, e.g., rodent cells, e.g., mouse or rat cells, rabbit cells, or pig cells.

An "intermediate length GAA repeat", as used herein, refers to a series of GAA trinucleotide repeats which are present in the first intron of the frataxin gene, and which range in number from 10, or about 10, to 36 or about 36 GAA repeats. These intermediate length GAA repeats are not generally found in normal alleles, nor are they found in alleles from FRDA patients.

As used herein, a "polymorphism" refers to the simultaneous occurrence in the population, of genomes showing allelic variations. Allelic variations can be seen in either alleles producing different phenotypes or, for example, changes in the DNA affecting an allele's restriction pattern.

As used herein, "non insulin diabetes mellitus" or "NIDDM" refers to a clinically heterogeneous disorder characterized by insulin resistance in peripheral tissues combined with impaired insulin secretion of the pancreatic β-cells. NIDDM is described in DeFronzo, R. A. et al. (1992) *Diabetes Care* 15:318–368, the contents of which are incorporated herein by reference.

An exogenously supplied cell, tissue, or cell product, e.g., a cytokine, as used herein, is a cell, tissue, or a cell product which is derived from an animal other than the one to which is supplied or administered. It can be from the same species or from different species than the animal to which it is supplied.

Culturing, as used herein, means contacting a cell or tissue with an environment which will support viability of the cell or tissue and which preferably supports proliferation of the cell or tissue.

A substantially purified preparation of cells, used herein, means a preparation of cells in which at least 50% of the cells, more preferably at least 70% of the cells, more preferably at least 80% of the cells, most preferably at least 90%, 95% or 99% of the cells of the subject cell.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

A "substantially pure nucleic acid" is a nucleic acid which is one or both of: not immediately contiguous with one or both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). The determination of percent homology between two sequences can be accomplished using a mathematical algorithim. A preferred, non-limiting example of a mathematical algorithim utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs of Altschul, et al. (1990) J. Mol. Biol. 215:403–10. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Programs which are equivalent in terms of the results they produce can be used.

As used herein, the term "transgene" means a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

"Misexpression", as used herein, refers to a non-wild type pattern of gene expression. It includes: expression at non-wild type levels, i.e., over, and particularly under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-transitional modification, stability, or biological activity of the expressed polypeptide; a pattern of expression that differs from wild type in terms of the effect of an environmental stimulus or extracellular stimulus on expression.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984);

the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Methods of the invention are useful for diagnosing risk for NIDDM. Risk for NIDDM, or other disorders characterized the presence of an intermediate GAA repeat, is diagnosed by determining if a subject, e.g., a human, carries an intermediate GAA repeat in the frataxin gene. The method is made possible, in part, by the discovery of the association of the intermediate GAA repeat with NIDDM.

Other features and advantages of the invention will be apparent from the following detailed description, and from the claims.

DETAILED DESCRIPTION

The drawings are first briefly described.

BRIEF DESCRIPTION OF THE DRAWINGS

FIGS. 1A–1B are a depiction of a box plot graph showing the size of repeat expansions found in two different populations (German [A] and U.S. [B]), separated for NIDDM patients versus control subjects. The horizontal lines within boxes indicate the median value for each group, the box covers interquartile distance (25th to 75th percentile), bars indicate 1.5-fold range of interquartile distance, circles indicate threefold range of interquartile distance, and stars indicate values outside threefold interquartile distance. Statistical significance was calculated using the Mann-Whitney U test.

FIGS. 2A–2B are a depiction of allele size distribution.

FRATAXIN GENE AND NIDDM

While an increased prevalence of diabetes among FRDA patients has been known for decades, the cloning of an intronic GAA repeat in the X25/frataxin gene causing FRDA (Campuzano, V. et al. (1996) *Science* 271:1423–1427) made it possible to evaluate a possible association between NIDDM and this genetic locus by direct assessment of the X25/ffrataxin polymorphism. Data presented herein show that an intermediate expansion of this GAA repeat tract is involved in the pathogenesis in up to 25% of patients with NIDDM. Thus, a heterozygous repeat expansion, shorter than that found in first-degree relatives of FRDA patients, is significantly associated with NIDDM in two separate populations. As indicated by the odds ratios, individuals carrying an intermediately expanded allele have a three- to four-fold increased risk of developing NIDDM, compared with individuals with normal alleles. The GAA repeat lengths found in these diabetic subgroups ranged from 10 to 36. Similar intermediate expansions were rarely found in the control groups, and in cases larger than $(GAA)_n=14$, these control subjects were younger than 45 years of age, and thus still at a significant likelihood of developing NIDDM in later years (Kahn, C. R. et al. (1996) *Annu. Rev. Med.* 47:509–531; McCarthy, M. I. et al. (1994) *Diabetologia* 37:959–968).

Frataxin is a small protein that is targeted to the mitochondria while sharing a conserved $NH_2$-terminal region with other proteins involved in mitochondrial metabolism (Koutnikova, H. et al. (1997) *Nat. Genet.* 16:345–351). An involvement in cellular iron metabolism has been repeatedly demonstrated for the frataxin gene product (Rotig, A. et al. (1997) *Nat. Genet.* 17:215–217; Babcock, M. et al. (1997) *Science* 276:1709–1712; Wilson, R. B. and D. M. Roof (1997) *Nat. Genet.* 16:352–357). Thus, frataxin appears to represent an endogenous antioxidant, as supported by additional observations (Ouahchi, K. et al. (1995) *Nat. Genet.* 9:141–145).

Recently it has been demonstrated that homozygous expansions of frataxin, as found in FRDA patients, lead to a lack of frataxin expression, presumably affecting neuronal and cardiomyocyte function in these patients (Campuzano, V. et al. (1997) *Hum. Mol. Genet.* 6:1771–1780). Since the level of frataxin expression seems to be inversely correlated with expansion size, we would predict a mild decrease in frataxin expression in the expanded NIDDM group described in this study. Clearly, frataxin deficiency alone is insufficient to cause NIDDM, since the majority of FRDA patients do not suffer from diabetes (Finocchiaro, G. et al. (1988) *Neurology* 38:1292–1296). On the other hand, a deficiency of frataxin due to an intronic repeat expansion appears to be a highly prevalent genetic cofactor in the pathogenesis of NIDDM.

Inherited tocopherol transport defects causing vitamin E deficiency in humans lead to a phenotype similar to that seen in FRDA patients (Ouahchi, K. et al. (1995) *Nat. Genet.* 9:141–145), indicating that frataxin may be an endogenously produced antioxidant protein. If this is the case, lack of this antioxidant may be involved in β-cell damage and increased lipid peroxidation, two factors known to be involved in the pathogenesis of NIDDM (Kahn, C. R. (1994) *Diabetes* 43:1066–1084).

Genetic Screening

The invention provides a method for detecting the presence of a frataxin intermediate GAA repeat length polymorphism in a biological sample, e.g., a biological sample derived from a subject at risk for developing diabetes, e.g., NIDDM. The method involves contacting the biological sample with a compound or an agent capable of detecting a frataxin intermediate GAA repeat length polymorphism, such that the presence of a frataxin intermediate GAA repeat length polymorphism is detected in the biological sample. A preferred agent for detecting a frataxin intermediate GAA repeat length polymorphism is a labeled or labelable nucleic acid probe capable of hybridizing to a frataxin mRNA containing an intermediate GAA repeat length polymorphism. The nucleic acid probe can be, for example, the full-length frataxin gene or a portion thereof, such as an oligonucleotide of at least 15, 30, 50, 100, 250 or 500 nucleotides in length and sufficient to specifically hybridize under appropriate conditions to a frataxin mRNA containing an intermediate GAA repeat length polymorphism.

The term "labeled or labelable", with regard to the probe, is intended to encompass direct labeling of the probe by coupling (i.e., physically linking) a detectable substance to the probe antibody, as well as indirect labeling of the probe by reactivity with another reagent that is directly labeled. The term "biological sample" is intended to include tissues, cells and biological fluids isolated from a subject, as well as tissues, cells and fluids present within a subject. That is, the detection method of the invention can be used to detect a frataxin intermediate GAA repeat length polymorphism in a biological sample in vitro as well as in vivo. For example, in vitro techniques for detection of a frataxin intermediate GAA repeat length polymorphism include Northern hybridizations and in situ hybridizations.

As described herein, there are a large number of assay techniques known in the art which can be used for detecting an intermediate GAA repeat length polymorphism in the frataxin gene. In certain embodiments, detection of the intermediate GAA repeat length polymorphism involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364). This method can include the steps of collecting a sample of cells from a subject, isolating nucleic acid (e.g., genomic, mRNA or both) from the cells of the sample, contacting the nucleic acid sample with one or more primers which specifically hybridize to a frataxin gene containing an intermediate GAA repeat length polymorphism under conditions such that hybridization and amplification of the frataxin intermediate GAA repeat length polymorphism (if present) occurs, and detecting the presence or absence of an amplification product, or detecting the size of the amplification product and comparing the length to a control sample.

Preferred primers for use in a polymerase chain reaction include primers GAA-104F (5' GGCTTAAACTTCCCA-CACGTGTT 3') (SEQ ID NO:1) and GAA-629R (5' AGGACCATCATGGCCACACTT 3') (SEQ ID NO:2). These primers flank the GAA repeat and generate a PCR product of 500+3n bp (n=number of GAA triplets) as described in, for example, Filla, A. et al. (1996) *Am. J. Hum. Genet.* 59:554–560, the contents of which are incorporated herein by reference.

In an alternative embodiment, the presence of a frataxin intermediate GAA repeat length polymorphism from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates the presence of an intermediate GAA repeat length polymorphism in the sample DNA. Moreover, the use of sequence specific ribozymes (see, for example, U.S. Pat. No. 5,498,531) can be used to score for the presence of intermediate GAA repeat length polymorphisms by development or loss of a ribozyme cleavage site.

In yet another embodiment, any of a variety of sequencing reactions known in the art can be used to directly sequence the frataxin gene and detect intermediate GAA repeat length polymorphisms by comparing the sequence of the sample being tested with the corresponding wild-type (control) sequence. Examples of sequencing reactions include those based on techniques developed by Maxam and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting intermediate GAA repeat length polymorphisms in the frataxin gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton (1993) *Mutat Res* 285:125–144; and Hayashi (1992) *Genet Anal Tech Appl* 9:73–79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting intermediate GAA repeat length polymorphisms include, selective oligonucleotide hybridization, selective amplification, and selective primer extension.

Kits

The invention also encompasses kits for detecting the presence of a frataxin intermediate GAA repeat length polymorphism in a biological sample. For example, the kit can include one or more of a labeled or labelable compound or agent capable of detecting a frataxin intermediate GAA repeat length polymorphism in a biological sample; means for determining the amount of a frataxin intermediate GAA repeat length polymorphism in the sample; and means for comparing the amount of a frataxin intermediate GAA repeat length polymorphism in the sample with a standard. The compound or agent can be packaged in a suitable container. The kit can further comprise instructions for using the kit to detect a frataxin intermediate GAA repeat length polymorphism.

Isolation of Nucleic Acid Molecules

In one embodiment, a nucleic acid molecule, e.g., DNA, total RNA, or mRNA, can be isolated from the biological sample obtained from the subject. For example, an initial crude cell suspension, such as may be obtained from dispersion of a biological sample, e.g., a tissue sample, is sonicated or otherwise treated to disrupt cell membranes so that a crude cell extract is obtained. Biochemical techniques, e.g., preferential precipitation of proteins, can be used for initial purification if desired. These techniques are described in, for example, Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The crude cell extract, or a partially purified RNA portion therefrom, can then be reated to further separate the RNA. For example, crude cell extract can be layered on top of a 5 ml cushion of 5.7 M CsCl, 10 mM Tris-HCl, pH 7.5, 1 mM EDTA in a 1 in.×3 ½ in. nitrocellulose tube and centrifuged in an SW27 rotor (Beckman Instruments Corp., Fullerton, Calif.) at 27,000 rpm for 16 hours at 15° C. After centrifugation, the tube contents are decanted, the tube is drained, and the bottom 0.5 cm containing the clear RNA pellet is cut off with a razor blade. The pellets are transferred to a flask and dissolved in 20 ml 10 mM Tris-HCl, pH 7.5, 1 mm EDTA, 5% sarcosyl and 5% phenol. The solution is then made 0.1 M in NaCl and shaken with 40 ml of a 1:1 phenol:chloroform mixture. RNA can be precipitated from the aqueous phase with ethanol in the presence of 0.2 M Na-acetate pH 5.5 and collected by centrifugation. Any other suitable method of isolating RNA from a cellular source, such as the Chomczynski method (described in U.S. Pat. No. 4,843,155) may be used.

The mRNA is usually isolated from the source cells under conditions which preclude degradation of the mRNA. The action of RNase enzymes is preferably inhibited because these enzymes are capable of hydrolytic cleavage of the RNA nucleotide sequence. A suitable method for inhibiting RNase during extraction from cells involves the use of 4 M guanidium thiocyanate and 1 M mercaptoethanol during the cell disruption step. In addition, a low temperature and a p.H. near 5.0 are helpful in further reducing RNase degradation of the isolated RNA.

In certain embodiments, the next step may be to form DNA complementary to the isolated heterogeneous sequences of mRNA. The enzyme of choice for this reaction is reverse transcriptase, although in principle any enzyme capable of forming a faithful complementary DNA copy of the mRNA template could be used. The cDNA transcripts produced by the reverse transcriptase reaction are somewhat heterogeneous with respect to sequences at the 5' end and the 3' end due to variations in the initiation and termination points of individual transcripts, relative to the mRNA template. The variability at the 5' end is thought to be due to the fact that the oligo-dT primer used to initiate synthesis is capable of binding at a variety of loci along the polyadenylated region of the mRNA. Synthesis of the CDNA transcript begins at an indeterminate point in the poly-A region, and variable length of poly-A region is transcribed depending on the initial binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

The following examples which further illustrate the invention should not be construed as limiting.

DETAILED DESCRIPTION OF THE INVENTION

Gene Therapy

Frataxin encoding nucleic acid can be used as a part of a gene therapy protocol to treat NIDDM or other disorder.

Expression constructs for frataxin, may be administered in any biologically effective carrier, e.g. any formulation or composition capable of effectively delivering frataxin encoding nucleic acid, or a sequence which promotes frataxin expression. Sequences which integrate and result in the deletion of al or part of a GAA can be used. Approaches include insertion of the subject gene into viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA encoding frataxin. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76,271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a polypeptide in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes.

In a representative embodiment, a gene encoding a polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic Helios gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). In a preferred embodiment of the invention, the Helios gene is targeted to hematopoietic cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

EXAMPLES

Materials and Methods

Subjects

Two populations, one from Germany and one from the U.S., were evaluated. The German group consisted of 186 people with NIDDM (age 62.5±12,6 years, BMI 28.9±5.6 kg/m, 93 men, 93 women) and 172 control subjects (age 53.2±15.8 years, BMI 27.1±4.9 kg/m, 88 men, 34 women). The U.S. group consisted of 165 individuals with NIDDM (age 63±6.3 years, BMI 30.3±6.2 kg/m2, 92 men 73 women) and 127 control subjects (age 53.2±17.1 years, BMI 25.2±4.1, 1 kg/m, 75 men, 52 women). All German subjects were Caucasian residents of Nordrhein-Westfalen, Germany; all U.S. subjects were Caucasian residents of Massachusetts. Control subjects consisted of employees of the participating institutions and spouses of NIDDM patients.

Phenotyping

Diabetes status was determined by oral glucose tolerance test using World Health Organization criteria and a Beckmann Glucose Analyzer II. Ataxia symptoms were excluded with a neurologic examination. Subjects with impaired glucose tolerance, but not diabetes, or ataxia-like symptoms on examination were excluded from the study. Furthermore, NIDDM subjects were only included when diabetes was diagnosed after the age of 20 years and treated with diet or oral antidiabetic agents for at least 2 years after diagnosis of diabetes.

Genotyping

Figure 2A:
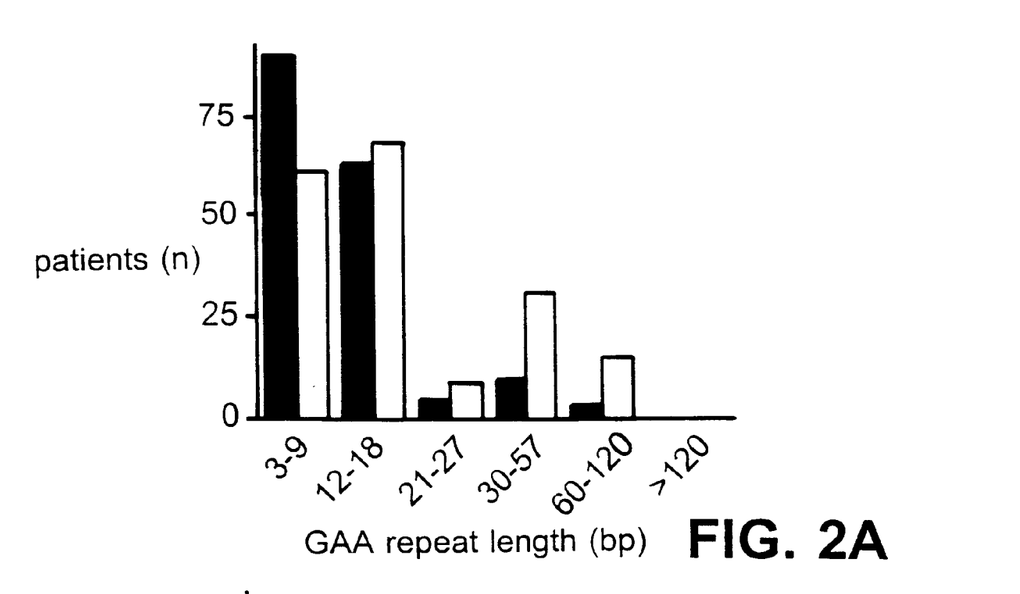
FIG. 2A is a depiction of the results for German subjects (■, control subjects; □, NIDDM patients)
Figure 2B:
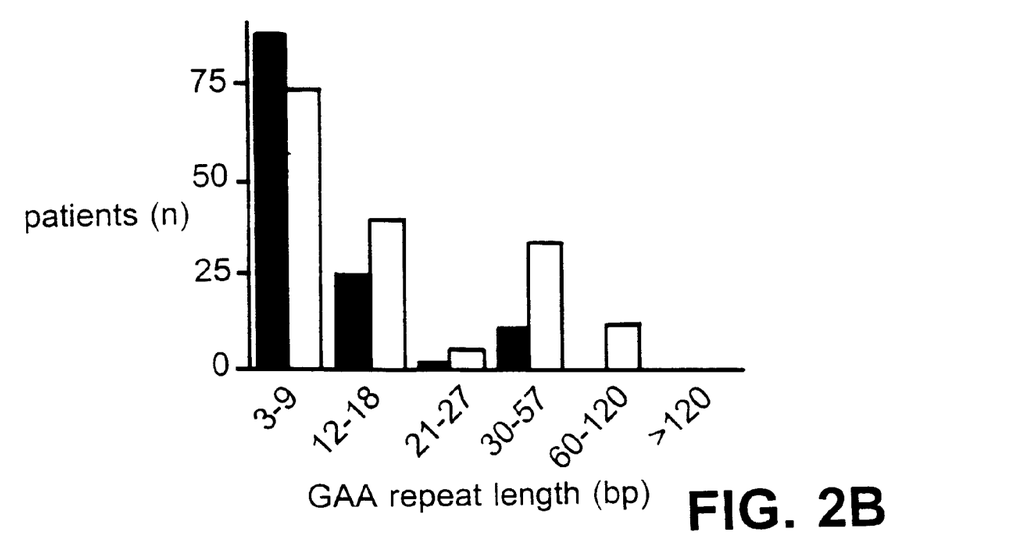
FIG. 2B is a depiction of the results for U.S. subjects (■, control subjects; □, NIDDM patients). The x-axis indicates groups of repeat lengths, and the y-axis indicates number of individuals. Filled bars indicate control subjects, and empty bars indicate NIDDM patients.

Genomic DNA was extracted from EDTA-stabilized blood. PCR primers and the PCR conditions were as described by Filla et al.(1996) *Am. J. Hum. Genet.* 59:554–560, except that Taq-Polymerase BioTherm was from GeneCraft (Muenster, Germany). Gel separation was performed under two different conditions. A first agarose gel (1.5%) was used for average size determination. For exact length determination, separation was performed on 4% agarose gels at 30 V for 8 hours. Because heterozygous repeat expansions may be difficult to detect, a heterozygous positive control was included in every PCR. For small repeat elongations (as occurs in NIDDM patients), a 50-base pair (bp) ladder (Gibco, Gaithersburg, Md.) was used to obtain exact length determination. The estimated error for repeat expansion determination was ±3 bp for nonexpanded and ±6 bp for intermediate expanded alleles. The gene was defined as intermediately expanded when it contained >27 bp and <120 bp, as recommended by Epplen et al. (1997) *Hum. Genet.* 99:834–836 and confirmed by data obtained herein (see FIG. 2). Borderline expanded alleles were cloned into pCR2.1 (Invitrogen, Carlsbad) and automatically sequenced (ABI. Foster City) for the exact determination of their length.

Statistical Analysis

Statistical analyses were performed with *Statistical Package for Social Studies* for Windows, release 7.5 NIDDM and control groups were evaluated separately for German and U.S. populations by $x^2$ and Mann-Whitney U tests (as described in Mann, H. B. et al. (1947) *Ann. Math. Statist.* 18:50–60) comparing normal and intermediately expanded subgroups. Box plot characteristics are as suggested by Tukey (1970) *Exploratory data analysis,* Reading, Mass., Addison-Wellesley.

Example 1

Determination of the Length of the Intronic GAA Repeat

To determine the length of the intronic GAA repeat, genomic DNA samples were evaluated using a PCR-based assay. This assay was expected to generate a product of 525 bp for non-expanded alleles and appropriately larger alleles for those containing expansions (Filla, A. et al. (1996) *Am. J. Hum. Genet.* 59:554–560). To determine the sensitivity of this assay to detect expanded alleles, genomic DNA from an FRDA patient predicted to carry two expanded alleles and from two first-degree relatives of this patient putatively carrying one expanded allele and one normal allele each were amplified. The FRDA patient was shown to carry two fully expanded alleles (Epplen, C. et al. (1997) *Hum. Genet.* 99:834–836), while the relatives carrying one normal and one fully expanded allele each, were easily distinguishable on the low-percentage screening gel (1.5% agarose). As predicted, while no signal was detected in the negative control, DNA samples derived from the 650 study subjects were amplified and evaluated using the same approach. The majority of NIDDM patients and almost all matched control subjects showed a normal allele size. However, approximately 25% of NIDDM patients showed a heterozygous intermediate expansion of the GAA repeat tract.

Figure 1A:
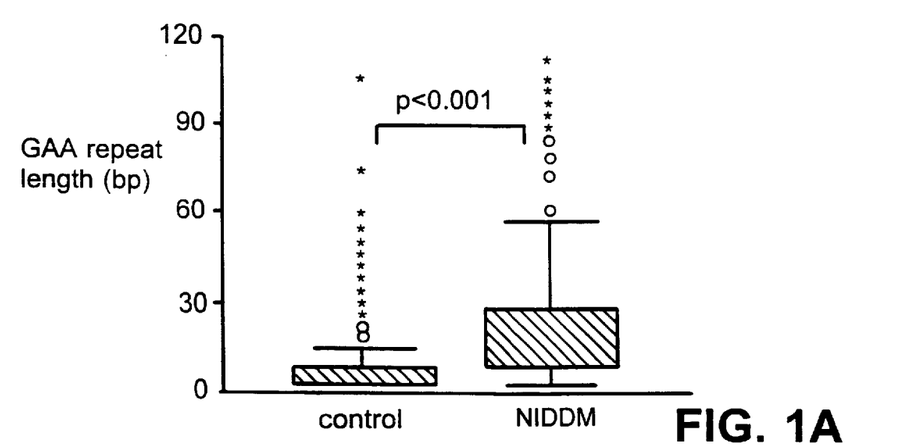
Figure 1B:
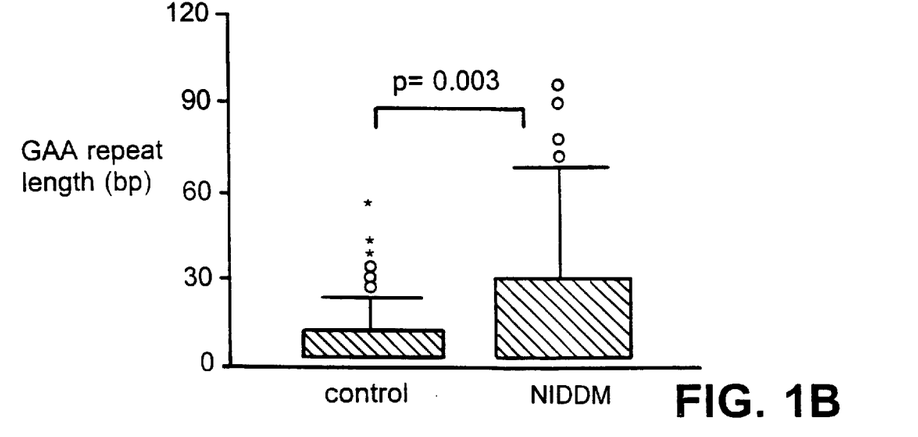

The exact size of the repeat was determined by subsequent high-percentage gels and sequencing. The distribution of intron repeat length was evaluated for the German and U.S. populations separately. The average length for the longer of both alleles was 22.3 bp (SD 23.1) for the German NIDDM patients vs. 9.9 bp (SD 13.3) for the German control subjects and 19.4 bp (SD 21.4) for the U.S. diabetic patients vs. 9.8 bp (SD 9.1) for the U.S. control subjects (see FIG. 1). No expansion typical of FRDA [$(GAA)_n$>65 or 195 bp] was found. Statistical evaluation using the Mann-Whitney U test (Mann, H. B. et al. (1947) *Ann. Math. Statist.* 18:50–60) indicated a significance of P<0.001 for the German study and P=0.003 for the U.S. study when NIDDM patients were compared with control subjects.

Two recent studies have described the prevalence of intermediate expansions in the general population and suggested a cutoff of 27 bp, i.e., $(GAA)_n$=9 (Epplen, C. et al. (1997) *Hum. Genet.* 99:834–836), to distinguish between normal and intermediately expanded alleles. Indeed, the allele distribution in our study exactly reflects the overall prevalence as described by Epplen et al. (Epplen, C. et al. (1997) *Hum. Genet.* 99:834–836) and Cossee et al. (Cossee, M. et al. (1997) *PNAS* 94:7452–7457) (see FIG. 2). In addition, in both populations studied we found that the size of 27 bp distinguished between normal and intermediately expanded groups as previously described. Based on this cutoff size of $(GAA)_n$=9, a shift toward intermediate expansions in both German and U.S. NIDDM subgroups was seen (see FIG. 2). While in total, 112 intermediately expanded alleles were found among all 650 samples, these intermediate expansions were present in 24.7% (n=46) of German NIDDM patients vs. 7.6% (n=13) of German control subjects and in 27.3% (n=45) of U.S. diabetic patients vs. 6.3% (n=8) of U.S. control subjects. Evaluation by $X^2$ tests revealed high substances, indicated by P values of <0.001 for both German and U.S. populations and an odds ratio of 3.36 (95% CI 1.72–6.55) for the German group and 4.01 (2.08–7.74) for the U.S. group. Further evaluation of the intermediately expanded compared with the nonexpanded subgroups revealed no significant correlation between age, sex, or BMI of patients or control subjects and allele length.

EQUIVALENTS

Those skilled in the art will recognize, or be able to ascertain, using no more than routine experimentation, many equivalents to the specific embodiments of the invention described herein. Such equivalents are intended to be encompassed by the following claims.

---

---

What is claimed is:

1. A method for determining whether a human subject is at risk for non-insulin dependent diabetes mellitus (NIDDM) comprising:

obtaining a biological sample from said subject; and detecting the presence or absence of an intermediate GAA repeat length polymorphism of 10 to 36 repeats in a frataxin gene in said biological sample, wherein the presence of an intermediate GAA repeat length polymorphism of 10 to 36 repeats in the frataxin gene indicates higher risk for NIDDM than does the absence of the polymorphism, thereby determining whether said subject is at risk for NIDDM.

2. The method of claim 1, further comprising isolating a nucleic acid molecule from said biological sample.

3. The method of claim 2, wherein said nucleic acid molecule is DNA.

4. The method of claim 1, wherein the presence or absence of an intermediate GAA repeat length polymorphism in the frataxin gene is detected by the use of a polymerase chain reaction.

5. The method of claim 1, wherein the presence or absence of an intermediate GAA repeat length polymorphism in the frataxin gene is detected by an alteration in a restriction enzyme cleavage pattern.

6. The method of claim 1, wherein the presence or absence of an intermediate GAA repeat length polymorphism in the frataxin gene is detected by nucleic acid sequencing.

7. The method of claim 1, wherein said biological sample is a biological fluid.

8. The method of claim 1, wherein said biological sample is a tissue sample.

9. The method of claim 1, wherein said biological sample is a cellular sample.

10. A method for determining whether a human subject is at risk for non-insulin dependent diabetes mellitus (NIDDM), comprising a DNA sample from the human subject with a nucleic acid probe, and detecting a frataxin intermediate GAA repeat length polymorphism of 10 to 36 repeats in the DNA sample, wherein the presence of an intermediate GAA repeat length polymorphism of 10 to 36 repeats in the frataxin gene indicates higher risk for NIDDM than dose the absence of the polymorphism, thereby determining if the subject is at risk for NIDDM.

11. The method of claim 10, wherein the nucleic acid probe is a labeled or unlabelled nucleic acid probe that hybridizes to frataxin DNA.

12. The method of claim 10, wherein the nucleic acid probe is a nucleic acid probe that amplifies a frataxin gene containing an intermediate length GAA repeat.

13. A kit for determining whether a human subject is at risk for non insulin dependent diabetes mellitus (NIDDM), comprising a nucleic acid probe that detects a frataxin intermediate GAA repeat length polymorphism of 10 to 36 repeats in a nucleic acid sample, and instructions for using the kit to determine if a subject is at risk for NIDDM.

14. The kit of claim 13, further comprising means for determining the amount of a frataxin intermediate GAA repeat length polymorphism in the sample and means for comparing the amount of a frataxin intermediate GAA repeat length polymorphism in the sample with a standard.

15. The kit of claim 13, wherein the nucleic acid probe is a labeled or unlabelable nucleic acid probe that hybridizes to frataxin DNA.

16. The kit of claim 13, wherein the nucleic acid probe is a nucleic acid probe that amplifies a frataxin gene containing an intermediate length GAA repeat.

* * * * *

UNITED STATES PATENT AND TRADEMARK OFFICE
CERTIFICATE OF CORRECTION

PATENT NO.    : 6,322,978 B1                                         Page 1 of 1
DATED         : November 27, 2001
INVENTOR(S)   : C. Ronald Kahn and Michael Ristow It is certified that error appears in the above-identified patent and that said Letters Patent is hereby corrected as shown below:

Column 1,
Line 15, before BACKGROUND OF INVENTION, insert the following paragraph:

-- STATEMENT REGARDING FEDERALLY SPONSORED RESEARCH
This invention was made with support from the U.S. government under grant number DK 36836 awarded by The National Institutes of Health. The government has certain rights in the invention. --.

Signed and Sealed this

Twenty-fifth Day of February, 2003

JAMES E. ROGAN
*Director of the United States Patent and Trademark Office*